United States Patent
Oslund

(10) Patent No.: US 11,202,705 B2
(45) Date of Patent: Dec. 21, 2021

(54) PARAVALVULAR LEAK PROTECTION

(71) Applicant: St. Jude Medical, Cardiology Division, Inc., St. Paul, MN (US)

(72) Inventor: John Oslund, Blaine, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 2 days.

(21) Appl. No.: 16/717,476

(22) Filed: Dec. 17, 2019

(65) Prior Publication Data

US 2020/0121455 A1 Apr. 23, 2020

Related U.S. Application Data

(60) Division of application No. 15/467,178, filed on Mar. 23, 2017, now Pat. No. 10,537,424, which is a continuation of application No. 13/797,481, filed on Mar. 12, 2013, now Pat. No. 9,636,222.

(51) Int. Cl.
*A61F 2/24* (2006.01)

(52) U.S. Cl.
CPC .......... *A61F 2/2418* (2013.01); *A61F 2/2409* (2013.01); *A61F 2/2436* (2013.01); *A61F 2210/0014* (2013.01); *A61F 2220/0075* (2013.01); *A61F 2250/003* (2013.01); *A61F 2250/0069* (2013.01)

(58) Field of Classification Search
CPC ..... A61F 2/2418; A61F 2/2409; A61F 2/2436
See application file for complete search history.

(56) References Cited

U.S. PATENT DOCUMENTS

| | | |
|---|---|---|
| 3,657,744 A | 4/1972 | Ersek |
| 4,275,469 A | 6/1981 | Gabbay |
| 4,491,986 A | 1/1985 | Gabbay |
| 4,759,758 A | 7/1988 | Gabbay |
| 4,878,906 A | 11/1989 | Lindemann et al. |
| 4,922,905 A | 5/1990 | Strecker |
| 4,994,077 A | 2/1991 | Dobben |
| 5,411,552 A | 5/1995 | Andersen et al. |

(Continued)

FOREIGN PATENT DOCUMENTS

| | | |
|---|---|---|
| DE | 19857887 A1 | 7/2000 |
| DE | 10121210 A1 | 11/2002 |

(Continued)

OTHER PUBLICATIONS

Braido et al., U.S. Appl. No. 29/375,243, filed Sep. 20, 2010, titled "Surgical Stent Assembly".

(Continued)

*Primary Examiner* — Jerrah Edwards
*Assistant Examiner* — Christine L Nelson
(74) *Attorney, Agent, or Firm* — Lerner, David, Littenberg, Krumholz & Mentlik, LLP

(57) ABSTRACT

A prosthetic heart valve includes a collapsible and expandable stent having a proximal end and a distal end, and a collapsible and expandable valve assembly, the valve assembly including a plurality of leaflets connected to at least one of the stent and a cuff. The heart valve further includes a conformable band disposed about the perimeter of the stent near the proximal end for filling gaps between the collapsible prosthetic heart valve and a native valve annulus.

18 Claims, 9 Drawing Sheets

(56) References Cited

U.S. PATENT DOCUMENTS

| | | |
|---|---|---|
| 5,480,423 A | 1/1996 | Ravenscroft et al. |
| 5,843,167 A | 12/1998 | Dwyer et al. |
| 5,855,601 A | 1/1999 | Bessler et al. |
| 5,935,163 A | 8/1999 | Gabbay |
| 5,961,549 A | 10/1999 | Nguyen et al. |
| 6,077,297 A | 6/2000 | Robinson et al. |
| 6,083,257 A | 7/2000 | Taylor et al. |
| 6,090,140 A | 7/2000 | Gabbay |
| 6,214,036 B1 | 4/2001 | Letendre et al. |
| 6,264,691 B1 | 7/2001 | Gabbay |
| 6,267,783 B1 | 7/2001 | Letendre et al. |
| 6,368,348 B1 | 4/2002 | Gabbay |
| 6,419,695 B1 | 7/2002 | Gabbay |
| 6,468,660 B2 | 10/2002 | Ogle et al. |
| 6,488,702 B1 | 12/2002 | Besselink |
| 6,517,576 B2 | 2/2003 | Gabbay |
| 6,533,810 B2 | 3/2003 | Hankh et al. |
| 6,582,464 B2 | 6/2003 | Gabbay |
| 6,610,088 B1 | 8/2003 | Gabbay |
| 6,623,518 B2 | 9/2003 | Thompson et al. |
| 6,685,625 B2 | 2/2004 | Gabbay |
| 6,719,789 B2 | 4/2004 | Cox |
| 6,730,118 B2 | 5/2004 | Spenser et al. |
| 6,783,556 B1 | 8/2004 | Gabbay |
| 6,790,230 B2 | 9/2004 | Beyersdorf et al. |
| 6,814,746 B2 | 11/2004 | Thompson et al. |
| 6,830,584 B1 | 12/2004 | Seguin |
| 6,869,444 B2 | 3/2005 | Gabbay |
| 6,893,460 B2 | 5/2005 | Spenser et al. |
| 6,908,481 B2 | 6/2005 | Cribier |
| 7,018,406 B2 | 3/2006 | Seguin et al. |
| 7,025,780 B2 | 4/2006 | Gabbay |
| 7,137,184 B2 | 11/2006 | Schreck |
| 7,160,322 B2 | 1/2007 | Gabbay |
| 7,247,167 B2 | 7/2007 | Gabbay |
| 7,267,686 B2 | 9/2007 | DiMatteo et al. |
| 7,311,730 B2 | 12/2007 | Gabbay |
| 7,374,573 B2 | 5/2008 | Gabbay |
| 7,381,218 B2 | 6/2008 | Schreck |
| 7,452,371 B2 | 11/2008 | Pavcnik et al. |
| 7,510,572 B2 | 3/2009 | Gabbay |
| 7,524,331 B2 | 4/2009 | Birdsall |
| RE40,816 E | 6/2009 | Taylor et al. |
| 7,585,321 B2 | 9/2009 | Cribier |
| 7,682,390 B2 | 3/2010 | Seguin |
| 7,731,742 B2 | 6/2010 | Schlick et al. |
| 7,803,185 B2 | 9/2010 | Gabbay |
| 7,846,203 B2 | 12/2010 | Cribier |
| 7,846,204 B2 | 12/2010 | Letac et al. |
| 7,914,569 B2 | 3/2011 | Nguyen et al. |
| D648,854 S | 11/2011 | Braido |
| D652,926 S | 1/2012 | Braido |
| D652,927 S | 1/2012 | Braido et al. |
| D653,341 S | 1/2012 | Braido et al. |
| D653,342 S | 1/2012 | Braido et al. |
| D653,343 S | 1/2012 | Ness et al. |
| D654,169 S | 2/2012 | Braido |
| D654,170 S | 2/2012 | Braido et al. |
| D660,432 S | 5/2012 | Braido |
| D660,433 S | 5/2012 | Braido et al. |
| D660,967 S | 5/2012 | Braido et al. |
| D684,692 S | 6/2013 | Braido |
| 2002/0036220 A1 | 3/2002 | Gabbay |
| 2003/0023303 A1 | 1/2003 | Palmaz et al. |
| 2003/0050694 A1 | 3/2003 | Yang et al. |
| 2003/0130726 A1 | 7/2003 | Thorpe et al. |
| 2004/0049262 A1 | 3/2004 | Obermiller et al. |
| 2004/0093075 A1 | 5/2004 | Kuehne |
| 2004/0210304 A1 | 10/2004 | Seguin et al. |
| 2005/0096726 A1 | 5/2005 | Sequin et al. |
| 2005/0137695 A1 | 6/2005 | Salahieh et al. |
| 2005/0137697 A1 | 6/2005 | Salahieh et al. |
| 2005/0256566 A1 | 11/2005 | Gabbay |
| 2006/0008497 A1 | 1/2006 | Gabbay |
| 2006/0058872 A1 | 3/2006 | Salahieh et al. |
| 2006/0074484 A1 | 4/2006 | Huber |
| 2006/0122692 A1 | 6/2006 | Gilad et al. |
| 2006/0149360 A1 | 7/2006 | Schwammenthal et al. |
| 2006/0173532 A1 | 8/2006 | Flagle et al. |
| 2006/0178740 A1 | 8/2006 | Stacchino et al. |
| 2006/0206202 A1 | 9/2006 | Bonhoeffer et al. |
| 2006/0241744 A1 | 10/2006 | Beith |
| 2006/0241745 A1 | 10/2006 | Solem |
| 2006/0259120 A1 | 11/2006 | Vongphakdy et al. |
| 2006/0259136 A1 | 11/2006 | Nguyen et al. |
| 2006/0259137 A1 | 11/2006 | Artof et al. |
| 2006/0265056 A1 | 11/2006 | Nguyen et al. |
| 2006/0276813 A1 | 12/2006 | Greenberg |
| 2007/0010876 A1 | 1/2007 | Salahieh et al. |
| 2007/0027534 A1 | 2/2007 | Bergheim et al. |
| 2007/0043435 A1 | 2/2007 | Seguin et al. |
| 2007/0055358 A1 | 3/2007 | Krolik et al. |
| 2007/0067029 A1 | 3/2007 | Gabbay |
| 2007/0073387 A1 | 3/2007 | Forster et al. |
| 2007/0093890 A1 | 4/2007 | Eliasen et al. |
| 2007/0100435 A1 | 5/2007 | Case et al. |
| 2007/0118210 A1 | 5/2007 | Pinchuk |
| 2007/0213813 A1 | 9/2007 | Von Segesser et al. |
| 2007/0233228 A1 | 10/2007 | Eberhardt et al. |
| 2007/0244545 A1 | 10/2007 | Birdsall et al. |
| 2007/0244552 A1 | 10/2007 | Salahieh et al. |
| 2007/0288087 A1 | 12/2007 | Fearnot et al. |
| 2008/0021552 A1 | 1/2008 | Gabbay |
| 2008/0039934 A1 | 2/2008 | Styrc |
| 2008/0071369 A1 | 3/2008 | Tuval et al. |
| 2008/0082164 A1 | 4/2008 | Friedman |
| 2008/0097595 A1 | 4/2008 | Gabbay |
| 2008/0114452 A1 | 5/2008 | Gabbay |
| 2008/0125853 A1 | 5/2008 | Bailey et al. |
| 2008/0140189 A1 | 6/2008 | Nguyen et al. |
| 2008/0147183 A1 | 6/2008 | Styrc |
| 2008/0154355 A1 | 6/2008 | Benichou et al. |
| 2008/0154356 A1 | 6/2008 | Obermiller et al. |
| 2008/0243245 A1 | 10/2008 | Thambar et al. |
| 2008/0255662 A1 | 10/2008 | Stacchino et al. |
| 2008/0262602 A1 | 10/2008 | Wilk et al. |
| 2008/0269879 A1 | 10/2008 | Sathe et al. |
| 2009/0062841 A1 | 3/2009 | Amplatz et al. |
| 2009/0112309 A1 | 4/2009 | Jaramillo et al. |
| 2009/0138079 A1 | 5/2009 | Tuval et al. |
| 2009/0192591 A1 | 7/2009 | Ryan et al. |
| 2010/0004740 A1 | 1/2010 | Seguin et al. |
| 2010/0036484 A1 | 2/2010 | Hariton et al. |
| 2010/0049306 A1 | 2/2010 | House et al. |
| 2010/0049313 A1* | 2/2010 | Alon .................... A61F 2/2418 623/2.11 |
| 2010/0087907 A1 | 4/2010 | Lattouf |
| 2010/0131055 A1 | 5/2010 | Case et al. |
| 2010/0168778 A1 | 7/2010 | Braido |
| 2010/0168839 A1 | 7/2010 | Braido et al. |
| 2010/0168844 A1 | 7/2010 | Toomes et al. |
| 2010/0185277 A1 | 7/2010 | Braido et al. |
| 2010/0191326 A1 | 7/2010 | Alkhatib |
| 2010/0204781 A1 | 8/2010 | Alkhatib |
| 2010/0204785 A1 | 8/2010 | Alkhatib |
| 2010/0217382 A1 | 8/2010 | Chau et al. |
| 2010/0249911 A1 | 9/2010 | Alkhatib |
| 2010/0249923 A1 | 9/2010 | Alkhatib et al. |
| 2010/0286768 A1 | 11/2010 | Alkhatib |
| 2010/0298931 A1 | 11/2010 | Quadri et al. |
| 2011/0029072 A1 | 2/2011 | Gabbay |
| 2011/0066237 A1 | 3/2011 | Matheny |
| 2013/0018458 A1 | 1/2013 | Yohanan et al. |
| 2014/0155997 A1 | 6/2014 | Braido |
| 2014/0194981 A1 | 7/2014 | Menk et al. |
| 2014/0222144 A1* | 8/2014 | Eberhardt .............. A61F 2/2409 623/2.38 |

FOREIGN PATENT DOCUMENTS

| | | |
|---|---|---|
| DE | 202008009610 U1 | 12/2008 |
| EP | 0122744 A1 | 10/1984 |
| EP | 0850607 A1 | 7/1998 |
| EP | 1000590 A1 | 5/2000 |

(56) References Cited

FOREIGN PATENT DOCUMENTS

| EP | 1360942 | A1 | 11/2003 |
|---|---|---|---|
| EP | 1584306 | A1 | 10/2005 |
| EP | 1598031 | A2 | 11/2005 |
| EP | 2047824 | A1 | 4/2009 |
| FR | 2850008 | A1 | 7/2004 |
| FR | 2847800 | B1 | 10/2005 |
| WO | 9117720 | A1 | 11/1991 |
| WO | 9716133 | A1 | 5/1997 |
| WO | 9832412 | A2 | 7/1998 |
| WO | 9913801 | A1 | 3/1999 |
| WO | 0128459 | A1 | 4/2001 |
| WO | 200149213 | A3 | 7/2001 |
| WO | 0154625 | A1 | 8/2001 |
| WO | 0156500 | A2 | 8/2001 |
| WO | 0176510 | A2 | 10/2001 |
| WO | 0236048 | A1 | 5/2002 |
| WO | 0247575 | A2 | 6/2002 |
| WO | 03047468 | A1 | 6/2003 |
| WO | 06073626 | A2 | 7/2006 |
| WO | 2007071436 | A2 | 6/2007 |
| WO | 08070797 | A2 | 6/2008 |
| WO | 2008092101 | A2 | 7/2008 |
| WO | 2010008548 | A2 | 1/2010 |
| WO | 2010008549 | A1 | 1/2010 |
| WO | 2010096176 | A1 | 8/2010 |
| WO | 2010098857 | A1 | 9/2010 |
| WO | 2013033791 | A1 | 3/2013 |
| WO | 2013036167 | A1 | 3/2013 |

OTHER PUBLICATIONS

Catheter-implanted prosthetic heart valves, Knudsen, L.L., et al., The International Journal of Artificial Organs, vol. 16, No. 5 1993, pp. 253-262.
International Search Report and Written Opinion for Application No. PCT/US2013/078296 dated Apr. 4, 2014.
Is It Reasonable to Treat All Calcified Stenotic Aortic Valves With a Valved Stent?, 579-584, Zegdi, Rachid, MD, PhD et al., J. of the American College of Cardiology, vol. 51, No. 5, Feb. 5, 2008.
Quaden et al., "Percutaneous aortic valve replacement: resection before implantation", pp. 836-840, European J. of Cardio-thoracic Surgery, 27 (2005).
Ruiz, Carlos, Overview of PRE-CE Mark Transcatheter Aortic Valve Technologies, Euro PCR—dated May 25, 2010?
Transluminal Aortic Valve Placement, Moazami, Nader, et al., ASAIO Journal, 1996; 42:M381-M385.
Transluminal Catheter Implanted Prosthetic Heart Valves, Andersen, Henning Rud, International Journal of Angiology 7:102-106 (1998).
Transluminal implantation of artificial heart valves, Andersen, H. R., et al., European Heart Journal (1992) 13, 704-708.

* cited by examiner

PARAVALVULAR LEAK PROTECTION

CROSS REFERENCE TO RELATED APPLICATIONS

The present application is a divisional of U.S. patent application Ser. No. 15/467,178, filed Mar. 23, 2017, which is a continuation of U.S. patent application Ser. No. 13/797,481, filed Mar. 12, 2013, now U.S. Pat. No. 9,636,222, the disclosure of which is hereby incorporated herein by reference.

BACKGROUND OF THE INVENTION

The present invention relates in general to heart valve replacement and, in particular, to collapsible prosthetic heart valves. More particularly, the present invention relates to devices and methods for positioning and sealing of collapsible prosthetic heart valves.

Prosthetic heart valves that are collapsible to a relatively small circumferential size can be delivered into a patient less invasively than valves that are not collapsible. For example, a collapsible valve may be delivered into a patient via a tube-like delivery apparatus such as a catheter, a trocar, a laparoscopic instrument, or the like. This collapsibility can avoid the need for a more invasive procedure such as full open-chest, open-heart surgery.

Collapsible prosthetic heart valves typically take the form of a valve structure mounted on a stent. There are two types of stents on which the valve structures are ordinarily mounted: a self-expanding stent or a balloon-expandable stent. To place such valves into a delivery apparatus and ultimately into a patient, the valve must first be collapsed or crimped to reduce its circumferential size.

When a collapsed prosthetic valve has reached the desired implant site in the patient (e.g., at or near the annulus of the patient's heart valve that is to be replaced by the prosthetic valve), the prosthetic valve can be deployed or released from the delivery apparatus and re-expanded to full operating size. For balloon-expandable valves, this generally involves releasing the entire valve, and then expanding a balloon positioned within the valve stent. For self-expanding valves, on the other hand, the stent automatically expands as the sheath covering the valve is withdrawn.

SUMMARY OF THE INVENTION

In some embodiments, a prosthetic heart valve includes a collapsible and expandable stent having a proximal end and a distal end, a cuff coupled to the stent, a valve assembly including a plurality of leaflets coupled to at least one of the stent or the cuff and a conformable band having an inner surface disposed near the perimeter of the stent adjacent the plurality of leaflets and an outer surface adapted for contacting body tissue, the conformable band being configured to seal the valve assembly against leakage by filling gaps between the prosthetic heart valve and the body tissue.

In some embodiments, a method of sealing a prosthetic heart valve in a patient includes positioning the prosthetic heart valve within body tissue, the prosthetic heart valve comprising (i) a collapsible and expandable stent, (ii) a valve assembly including a plurality of leaflets coupled to the stent and (iii) a conformable band having an inner surface disposed about the plurality of leaflets and an outer surface adapted for contacting body tissue, and expanding the stent until the conformable band is in sealing contact with the body tissue. In some embodiments, a prosthetic heart valve includes a collapsible and expandable stent having a proximal end and a distal end, a valve assembly including a plurality of leaflets coupled to the stent, and a conformable band disposed about the stent between the proximal and distal ends thereof, the band adapted for creating a fluid seal about the circumference of the stent with an adjacent body tissue.

BRIEF DESCRIPTION OF THE DRAWINGS

Various embodiments of the present invention are described herein with reference to the drawings, wherein.

Various embodiments of the present invention will now be described with reference to the appended drawings. It is appreciated that these drawings depict only some embodiments of the invention and are therefore not to be considered limiting of its scope.

DETAILED DESCRIPTION OF THE INVENTION

Despite the various improvements that have been made to the collapsible prosthetic heart valve delivery process, conventional devices suffer from some shortcomings. For example, with conventional self-expanding valves, clinical success of the valve is dependent on accurate deployment and anchoring. Inaccurate deployment and anchoring of the valve increases risks such as valve migration, which may result in severe complications due to obstruction of the left ventricular outflow tract. Additionally, calcification of the aortic valve may affect performance and the interaction between the implanted valve and the calcified tissue is believed to be relevant to leakage as will be outlined below.

Moreover, anatomical variations between patients may require removal of a fully deployed heart valve from the patient if it appears that the valve is not functioning properly. Removing a fully deployed heart valve increases the length of the procedure and increases the risk of infection and/or damage to heart tissue. Thus, methods and devices are desirable that would reduce the likelihood of removal. Methods and devices are also desirable that would reduce the likelihood of valve leakage due to gaps formed between the implanted heart valve and patient tissue known as paravalvular leaks.

There therefore is a need for further improvements to the devices, systems, and methods for transcatheter delivery and positioning of collapsible prosthetic heart valves. Specifically, there is a need for further improvements to the devices, systems, and methods for accurately implanting a prosthetic heart valve. Among other advantages, the present invention may address one or more of these needs.

As used herein, the term "proximal," when used in connection with a prosthetic heart valve, refers to the end of the heart valve closest to the heart when the heart valve is implanted in a patient, whereas the term "distal," when used in connection with a prosthetic heart valve, refers to the end of the heart valve farthest from the heart when the heart valve is implanted in a patient. When used in connection with devices for delivering a prosthetic heart valve into a patient, the terms "trailing" and "leading" are to be taken as relative to the user of the delivery devices. "Trailing" is to be understood as relatively close to the user, and "leading" is to be understood as relatively farther away from the user.

Figure 1:
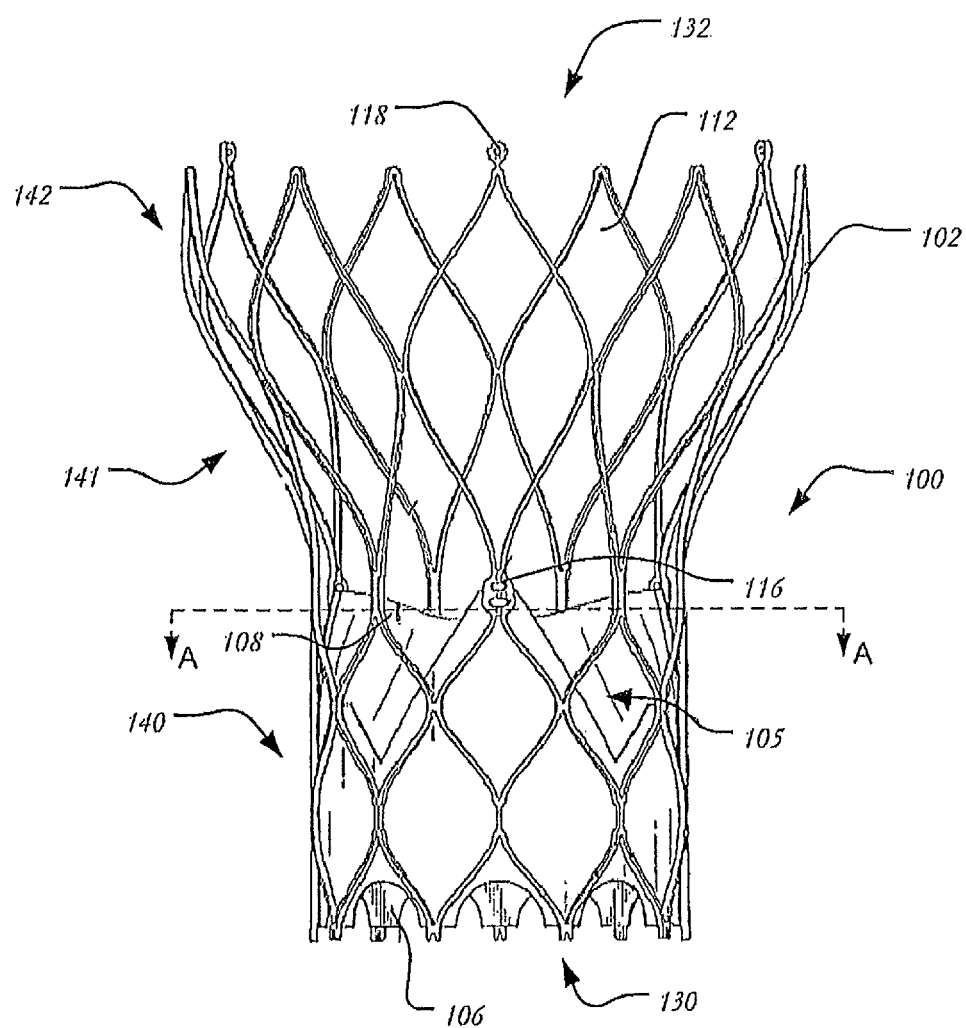
FIG. 1 is a side elevational view of a conventional prosthetic heart valve including a stent.

FIG. 1 shows a known collapsible stent-supported prosthetic heart valve 100 for use in accordance with the various embodiments of the present disclosure. The prosthetic heart valve 100 is designed to replace the function of a native aortic valve of a patient.

The prosthetic heart valve will be discussed in more detail with reference to FIG. 1. It will also be noted that while the inventions herein described are predominately discussed in terms of a tricuspid valve and a stent having a shape as illustrated in FIG. 1, the valve could be a bicuspid valve, such as the mitral valve, and the stent could have different shapes, such as a flared or conical annulus section, a less-bulbous aortic section, and the like, and a differently shaped transition section.

Prosthetic heart valve 100 includes an expandable stent 102 which may be formed from materials that are capable of self-expansion. Stent 102 extends from a proximal or annulus end 130 to a distal or aortic end 132, and includes an annulus section 140 adjacent the proximal end and an aortic section 142 adjacent the distal end. The annulus section 140 has a relatively small cross-section in the expanded condition, while the aortic section 142 has a relatively large cross-section in the expanded condition. Preferably, annulus section 140 is in the form of a cylinder having a substantially constant diameter along its length. A transition section 141 may taper outwardly from the annulus section 140 to the aortic section 142. Each of the sections of the stent 102 includes a plurality of cells 112 connected to one another in one or more annular rows around the stent. For example, as shown in FIG. 1, the annulus section 140 may have two annular rows of complete cells 112 and the aortic section 142 and transition section 141 may each have one or more annular rows of partial cells 112. The cells 112 in the aortic section 142 may be larger than the cells 112 in the annulus section 140. The larger cells in the aortic section 142 better enable the prosthetic valve 100 to be positioned without the stent structure interfering with blood flow to the coronary arteries.

Stent 102 may include one or more retaining elements 118 at the distal end 132 thereof, the retaining elements being sized and shaped to cooperate with female retaining structures (not shown) provided on the deployment device. The engagement of retaining elements 118 with the female retaining structures on the deployment device helps maintain prosthetic heart valve 100 in assembled relationship with the deployment device, minimizes longitudinal movement of the prosthetic heart valve relative to the deployment device during unsheathing or resheathing procedures, and helps prevent rotation of the prosthetic heart valve relative to the deployment device as the deployment device is advanced to the target location and during deployment.

The stent 102 may also include a plurality of commissure points 116 for attaching the commissure between two adjacent leaflets to the stent. As can be seen in FIG. 1, the commissure points 116 may lie at the intersection of four cells 112, two of the cells being adjacent one another in the same annular row, and the other two cells being in different annular rows and lying in end-to-end relationship. Preferably, commissure points 116 are positioned entirely within annulus section 140 or at the juncture of annulus section 140 and transition section 141. Commissure points 116 may include one or more eyelets which facilitate the suturing of the leaflet commissure to the stent.

The prosthetic heart valve 100 includes a valve assembly 105 positioned in the annulus section 140. Valve assembly 105 may be secured to stent 102 in the various manners described above. Valve assembly 105 includes a cuff 106 and a plurality of leaflets 108 which collectively function as a one-way valve by contacting one another. FIG. 1 illustrates a prosthetic heart valve for replacing a native tricuspid valve, such as the aortic valve. Accordingly, prosthetic heart valve 100 is shown in FIG. 1 with three leaflets 108, as well as three commissure points 116. However, it will be appreciated that the prosthetic heart valves according to this aspect of the invention may have a greater or lesser number of leaflets and commissure points.

Although cuff 106 is shown in FIG. 1 as being disposed on the lumenal or inner surface of annulus section 140, it is contemplated that the cuff may be disposed on the ablumenal or outer surface of annulus section 140, or may cover all or part of either or both of the lumenal and ablumenal surfaces of annulus section 140. Both the cuff 106 and the leaflets 108 may be wholly or partly formed of any suitable biological material or polymer, including those, such as PTFE, described above in connection with prosthetic heart valve 100.

As is shown in FIG. 1, in one example the entirety of valve assembly 105, including the leaflet commissures, is positioned in the annulus section 140 of stent 102. When opened, the leaflets may extend further into the transition region or may be designed such that they remain substantially completely within the annulus region. That is, substantially the entirety of valve assembly 105 is positioned between the proximal end 130 of stent 102 and the commissure points 116, and none of the valve assembly 105 is positioned between commissure points 116 and the distal end 132 of the stent.

In operation, the embodiments of the prosthetic heart valve described above may be used to replace a native heart valve, such as the aortic valve, a surgical heart valve or a heart valve that has undergone a surgical procedure. The prosthetic heart valve may be delivered to the desired site (e.g., near a native aortic annulus) using any suitable delivery device, including the delivery devices described in detail below. During delivery, the prosthetic heart valve is disposed inside the delivery device in the collapsed condition. The delivery device may be introduced into a patient using a transfemoral, transapical or transseptal approach. Once the delivery device has reached the target site, the user may deploy any of the prosthetic heart valves described above. Upon deployment, the prosthetic heart valve expands into secure engagement within the native aortic annulus. When the prosthetic heart valve is properly positioned inside the heart, it works as a one-way valve, allowing blood to flow in one direction and preventing blood from flowing in the opposite direction.

Problems may be encountered when implanting the prosthetic heart valve. For example, in certain procedures, collapsible valves may be implanted in a native valve annulus without first resecting the native valve leaflets. The collapsible valves may have critical clinical issues because of the nature of the stenotic leaflets that are left in place. Additionally, patients with uneven calcification, bi-cuspid aortic valve disease, and/or valve insufficiency could not be treated well, if at all, with the current collapsible valve designs.

The reliance on unevenly calcified leaflets for proper valve placement and seating could lead to several problems, such as paravalvular leakage (PV leak), which can have severely adverse clinical outcomes. To reduce these adverse events, the optimal valve would seal and anchor adequately without the need for excessive radial force that could harm nearby anatomy and physiology.

Figure 2:
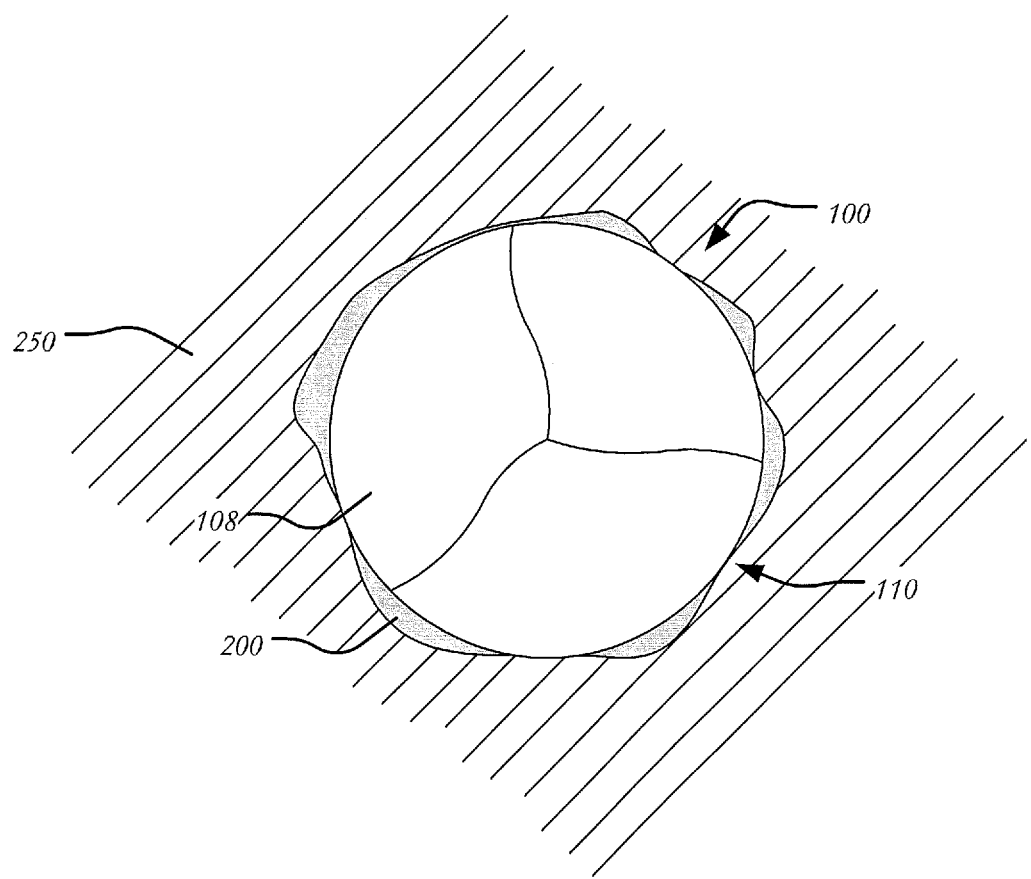
FIG. 2 is a cross-sectional schematic illustration of the prosthetic heart valve of FIG. 1 disposed within native valve annulus.

FIG. 2 is a cross-sectional illustration of prosthetic heart valve 100 having leaflets 108 disposed within native valve annulus 250, taken along line A-A shown in FIG. 1. As seen in FIG. 2, the substantially circular annulus section 110 of the stent 102 is disposed within a non-circular native valve annulus 250. At certain locations around the perimeter of heart valve 100, gaps 200 form between the heart valve 100 and the native valve annulus 250. Blood flowing through these gaps and around the valve assembly 105 of prosthetic heart valve 100 can result in leakage or regurgitation and other inefficiencies which can reduce cardiac performance. Such improper fitment may be due to suboptimal native valve annulus geometry due, for example, to calcification of the native valve annulus 250 or due to unresected native leaflets.

Figure 3A:
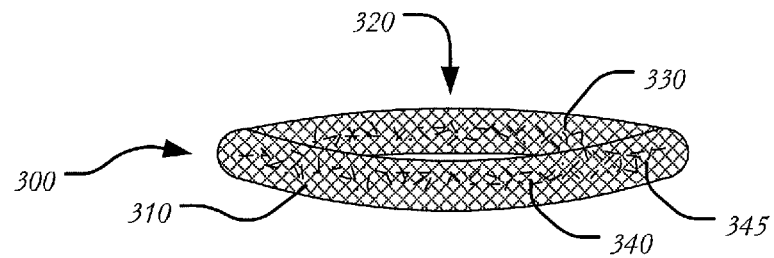
FIG. 3A illustrates one example of a conformable band in the shape of a toroid in accordance with one embodiment of the present invention.

FIG. 3A illustrates one embodiment of a conformable band 300 that would fill irregularities between the heart valve 100 and the native valve annulus 250. As will be described in more detail below, conformable band 300 allows for superior sealing between the perimeter of heart valve 100 and native valve annulus 250 while affording a low radial outward force.

Conformable band 300 may include a body 310 formed of a ring-like metallic structure in the shape of a toroid having an inner surface 330 defining a central aperture 320 for coupling to heart valve 100 and an outer surface 340 for contacting body tissue. In its relaxed condition, body 310 may have a diameter that is equal to or greater than the diameter of the annulus where it will be implanted. Body 310 of conformable band 300 may be flexible and capable of contracting in the radial direction when a force is applied thereto to conform to the shape of the annulus in which it will be implanted.

In one example, body 310 comprises a braided metal fabric that is both resilient and capable of heat treatment to substantially set a desired preset shape. One class of materials which meets these qualifications is shape memory alloys. One example of a shape memory alloy is Nitinol. It is also understood body 310 may comprise various materials other than Nitinol that have elastic and/or memory properties, such as spring stainless steel, trade named alloys such as Elgiloy®, Hastelloy®, CoCrNi alloys (e.g., trade name Phynox), MP35N®, CoCrMo alloys, or a mixture of metal and polymer fibers. Depending on the individual material selected, strand diameter, number of strands, and pitch may be altered to achieve the desired properties of body 310. Body 310 may be formed, for example, of a braided nitinol mesh and may include a shape-memory material or a superelastic material that is capable of collapsing and expanding to conform to patient vasculature. It is also contemplated that the body 310 can be constructed from bio-compatible polymer material. In at least some examples, body 310 may be hollow and/or loaded with a filler 345 of fabric or fibers of various materials that is intertwined and/or located within the mesh of the conformable band to assist with, sealing, occlusion and healing. For example, conformable band 300 may include a filler 345 of polyester threads or polyester fabric as well as any suitable implantable fiber material to increase density and/or promote tissue growth. Filler 345 may also include a foam material such as a closed cell sponge. The density of conformable band 300 may be such that it impedes the flow of blood through it. In at least some examples, conformable band 300 and/or filler 345 may be formed of a hydrophobic material that expands with moisture. Additionally, conformable band 300 and/or filler 345 may be configured from a hydrophobic material that expands upon blood contact.

Figure 3B:
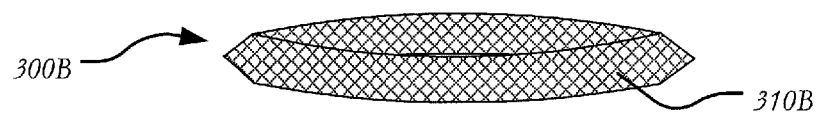
FIG. 3B illustrates another example of a conformable band in accordance with one embodiment of the present invention.
Figure 3C:
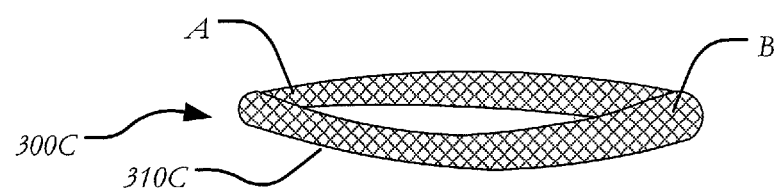
FIG. 3C illustrates another example of a conformable band in accordance with one embodiment of the present invention.

While conformable band 300 is shown in FIG. 3A as a toroid, it will be understood that varying shapes and/or sizes may be used to construct conformable band 300. For example, though body 310 has been described as ring-like, it will be understood that the perimeter of body 310 may likewise form an oval, a square or any other desirable polygon. The cross-sectional shape around the band 300 may also be varied in such shapes as a circular, oval, polygon, square, diamond, triangle, etc. For example, FIG. 3B illustrates a conformable band 300B constructed of a body 310B having a cross-sectional shape of a triangle revolved about a central axis to form a three-dimensional shape. Moreover, the cross-sectional height and/or width of certain portions of body 310 may be non-uniform in its relaxed condition as shown in FIG. 3C, where conformable band 300C includes a body 310C having portion "A" with a smaller cross-sectional height and width than portion "B." Additionally, conformable band 300 may be discontinuous about a perimeter. Thus, the term "band" does not limit the contemplated embodiments to constructions that are continuous about a perimeter.

Figure 4:
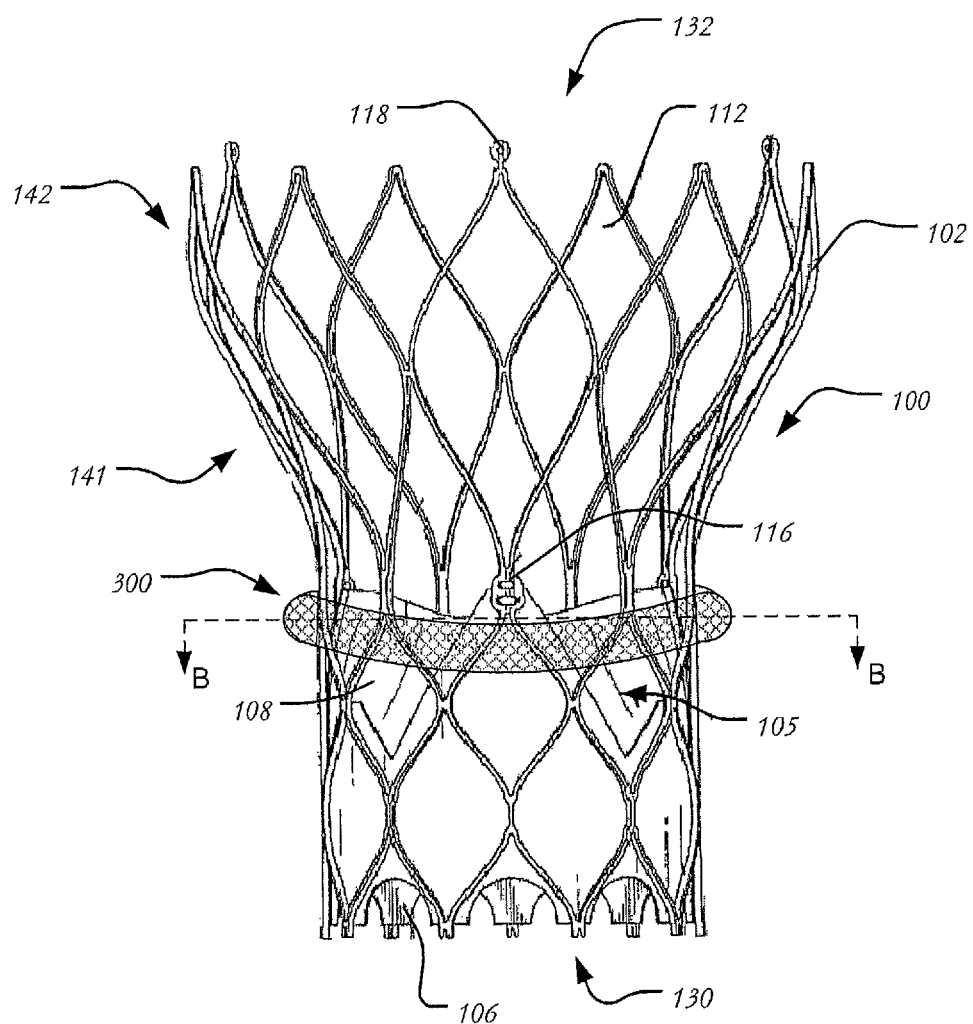
FIG. 4 is a side elevational view of a conventional prosthetic heart valve including a stent having a conformable band as shown in FIG. 3A.

FIG. 4 illustrates a conformable band 300 according to a first embodiment of the present invention disposed about the outer perimeter of heart valve 100. Conformable band 300 may be sewn, glued, welded, or otherwise coupled in any suitable manner to selected struts of stent 102. Alternatively, conformable band 300 may be coupled to the outside surface of cuff 106. In at least some examples, and as shown in FIG. 4, conformable band 300 may be coupled at the longitudinal level of the valve leaflets 108.

Figure 5A:
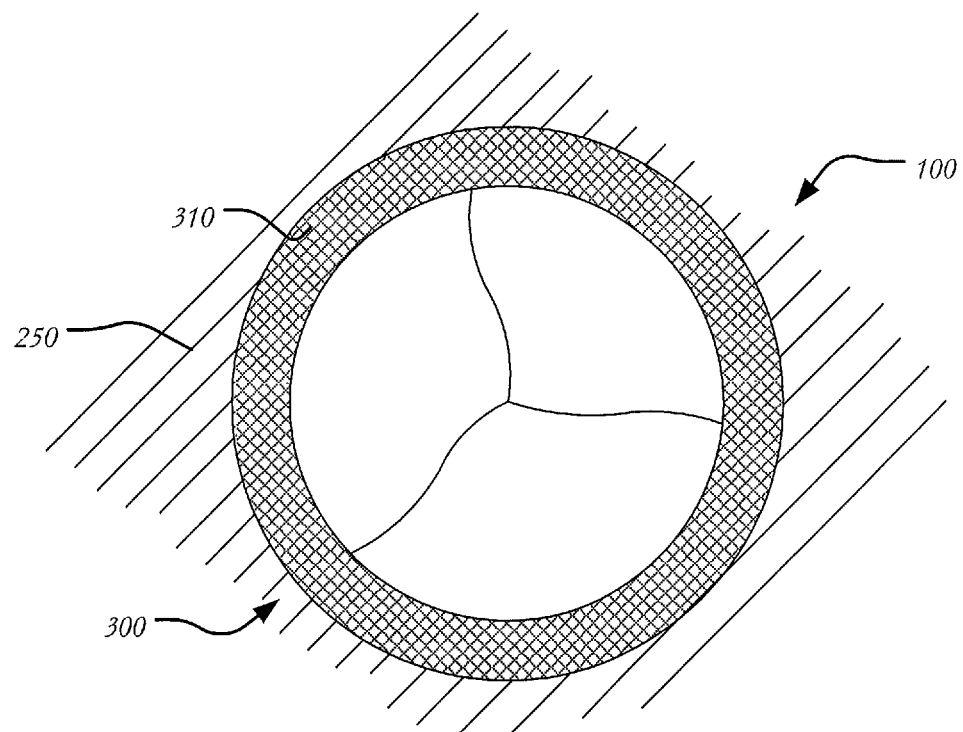
FIG. 5A is a cross-sectional schematic illustration of a prosthetic heart valve having a conformable band in its fully expanded state.

FIG. 5A illustrates a configuration in which the conformable band 300 is in its relaxed state where the body 310 has fully radially expanded. The mesh of conformable band 300 may be capable of promoting tissue growth between the heart valve 100 and the native valve annulus 250. In at least some examples, conformable band 300 may be treated with a biological or chemical agent to promote tissue growth on the conformable band, further sealing the heart valve within the native valve annulus.

Figure 5B:
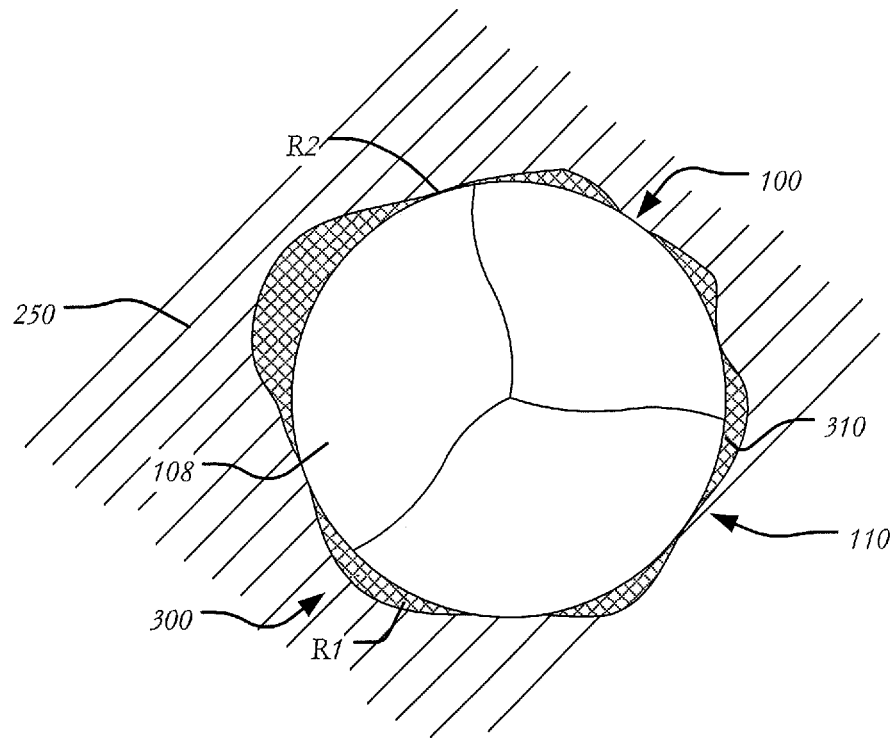
FIG. 5B is a cross-sectional schematic illustration of the prosthetic heart valve having a conformable band of FIG. 4 disposed within native valve annulus.

FIG. 5B is a cross-sectional illustration of prosthetic heart valve 100 having a conformable band 300 disposed within native valve annulus 250, taken along line B-B shown in FIG. 4. As seen in FIG. 5B, the annulus section 110 of the stent 102 is substantially circular and disposed within a non-circular native valve annulus 250. Conformable band 300 has contracted in certain regions to a radius less than the relaxed state radius and conformed to fill the gaps that were previously disposed between the outer surface of heart valve 100 and the native valve annulus 250. By way of illustration, at region R1 body 310 has contracted partially and at region R2 body 310 has almost fully contracted against the wall of prosthetic heart valve 100. With body 310 contracting to different amounts around the circumference, conformable band 300 is capable of sealing the irregular-sized gaps formed between heart valve 100 and native valve annulus 250.

Figure 6:
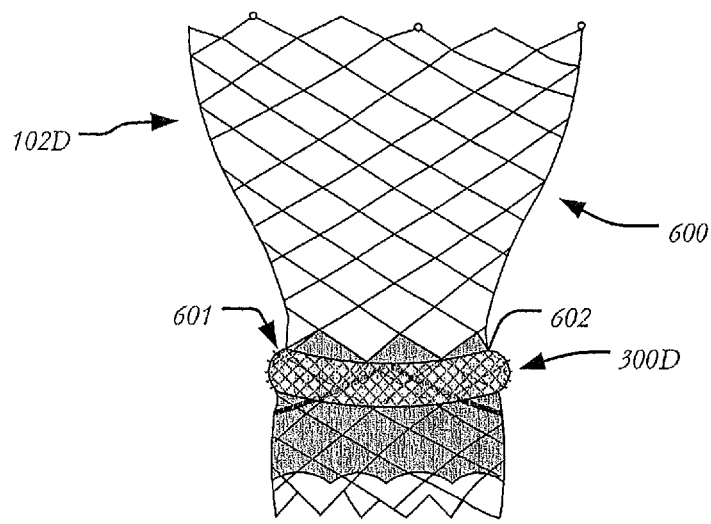
FIG. 6 is a schematic illustration of a conformable band as shown in FIG. 3A incorporated into a heart valve.

FIGS. 6 and 7 illustrate two further embodiments of the conformable band 300 with a heart valve 100. FIG. 6 illustrates a first variation where instead of being separately formed and disposed over stent 102 as in FIG. 4, conformable band 300D may be incorporated into stent 102. For example, heart valve 600 may include stent 102D having flared portion 601 capable of receiving conformable band 300D. Flared portion 601 may be annular and bulbous-shaped as shown in FIG. 6. Conformable band 300D may be coupled to selected struts 602 of stent 102D such that simultaneous delivery of stent 102D and conformable band 300D is possible.

Figure 7A:
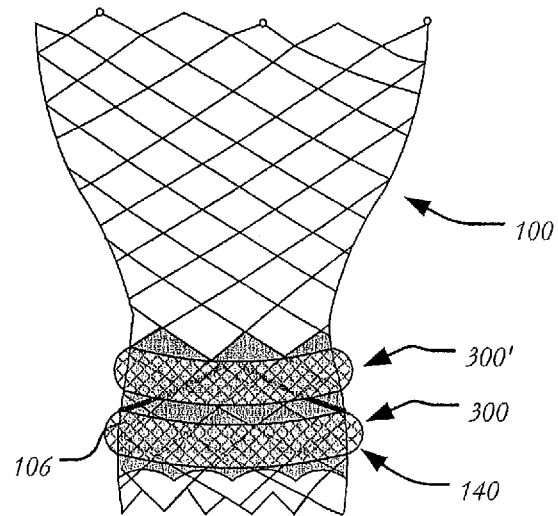
FIG. 7A is a schematic of a prosthetic heart valve having two conformable bands as shown in FIG. 3A arranged in different longitudinal positions near the annulus section of a heart valve in accordance with another embodiment of the present invention.

FIG. 7A illustrates a second variation of a prosthetic heart valve having two conformable bands 300, 300' arranged exteriorly in different longitudinal positions near the annulus section 140 of heart valve 100. It will be understood that any number of conformable bands may be used in conjunction with the contemplated device. Moreover, multiple conformable bands 300 may be incorporated interiorly into the stent as discussed above with reference to FIG. 6.

Figure 7B:
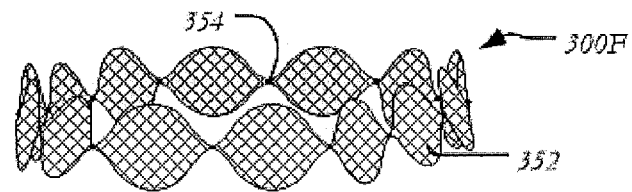
FIG. 7B is a schematic of an illustration of a conformable band configured as a beaded chain in accordance with another embodiment of the present invention.

FIG. 7B is a schematic illustration of another embodiment in which conformable band 300F is configured as a beaded chain. As seen in FIG. 7B, a plurality of beads 352 are connected to one another via junctions 354 to form a ring. Each bead 352 may be formed of any of the materials described above with reference to body 310 of FIG. 3A such as, for example, a nitinol mesh. Additionally, each bead 352 may be packed with a filler (not shown) as described above. Beads 352 may include a longitudinal cross-section that is lens or eye-shaped as shown in FIG. 7B, or oval, circular or any other suitable shape. Additionally, each bead may be generally round or may be dome-shaped having a substantially flat surface that contacts a valve assembly or cuff.

Figure 7C:
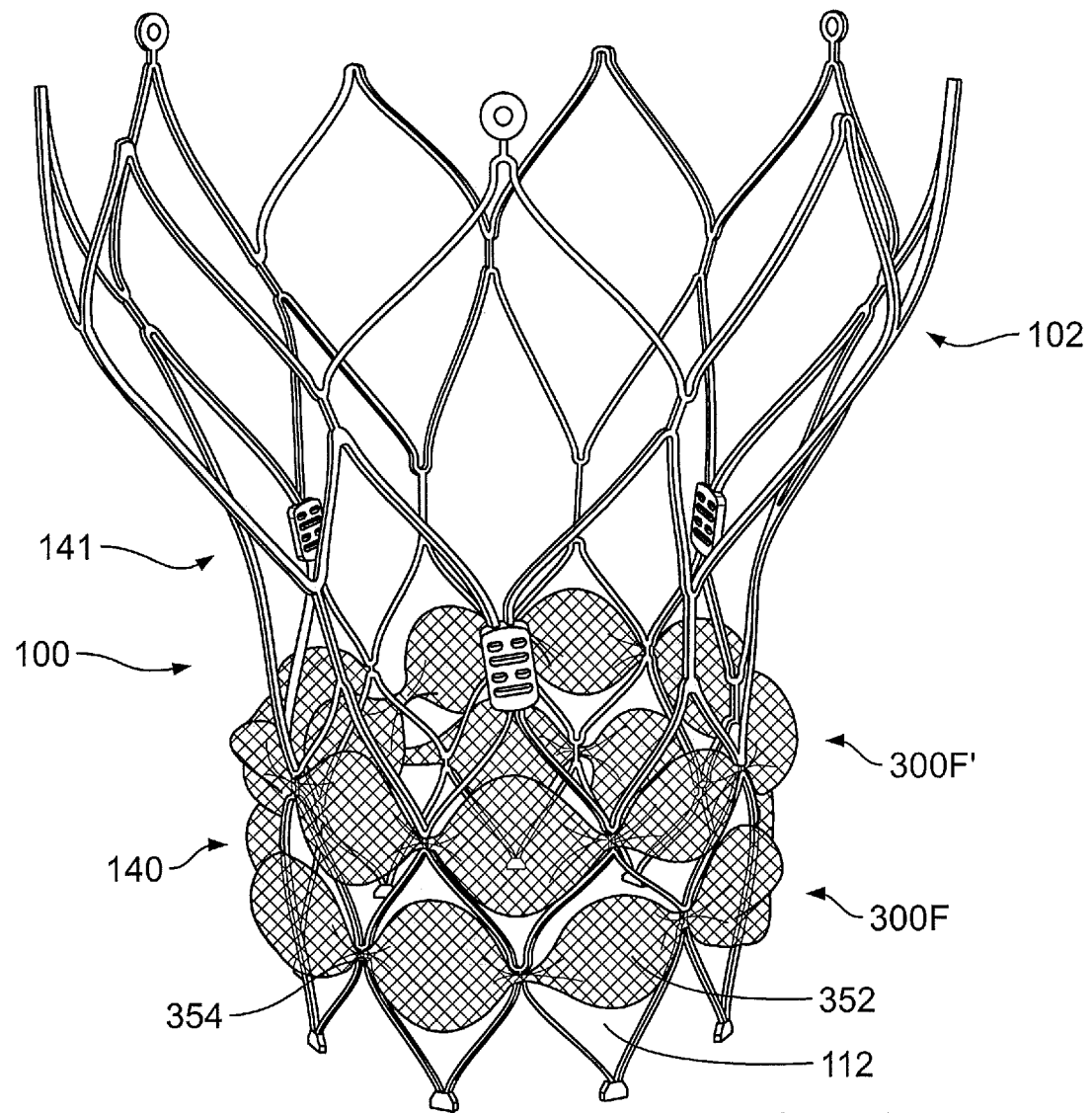
FIG. 7C is a photograph of the beaded chain of FIG. 7B disposed near the annulus section of a heart valve.

FIG. 7C is a photograph of conformable band 300F of FIG. 7B coupled to heart valve 100. For the sake of clarity, the valve assembly, including the cuff and leaflets, of heart valve 100 is not attached to stent 102. As seen in FIG. 7C, conformable band 300F is disposed over annulus section 140 of heart valve 100. A second conformable band 300F is disposed near annulus section 140, adjacent first conformable band 300F but closer to transition section 141. Focusing now on conformable band 300F, each bead 352 may be shaped to have a width that is substantially equal to the width of cell 112 in annulus section 140 and a length equal to about half of cell 112. Beads 352 may be connected to one another and spaced such that each bead 352 is positioned in the center of a given cell 112 around the perimeter of annulus section 140. Additionally, conformable band 300F may be configured such that at a given longitudinal position, a single bead 352 is disposed at each cell 112. Conformable band 300F is configured and positioned similar to conformable band 300F, although it will be noted that the two bands 300F, 300F are horizontally offset from one another due to the layout of cells 112 (e.g., the centers of beads 352 of conformable band 300F line up with junctions 354 of conformable band 300F).

FIGS. 8A-D illustrate the use of conformable band 300 and in a process of sealing a heart valve 100 within a native valve annulus 250. As an initial step, heart valve 100 having conformable band 300 may be disposed within a delivery catheter 400 (FIG. 8A) in a collapsed condition. Delivery catheter 400 may include an outer sheath 410 and an inner shaft 420, the outer sheath 410 being slidable relative to the inner shaft 420. An accepting member 430 may be affixed to inner end of inner shaft 420 and may include receiving elements (not shown) for accepting biased retaining elements 118 of the heart valve. Heart valve 100 may be coupled to inner shaft 420 at accepting member 430 via retaining elements 118. The catheter 400 may then be inserted into the patient, the heart valve 100 and conformable band 300 being in the collapsed condition, and advanced to the desired site for valve replacement. For example, for transfemoral insertion, heart valve 100 may be inserted into the patient's femoral artery and advanced intravascularly to the descending aorta and the site of the native aortic valve. If the heart valve 100 or catheter 400 includes echogenic materials, such materials may be used to guide the catheter to the appropriate position using the assistance of three-dimensional echocaradiography to visualize the heart valve 100 within the patient.

Figure 8A:
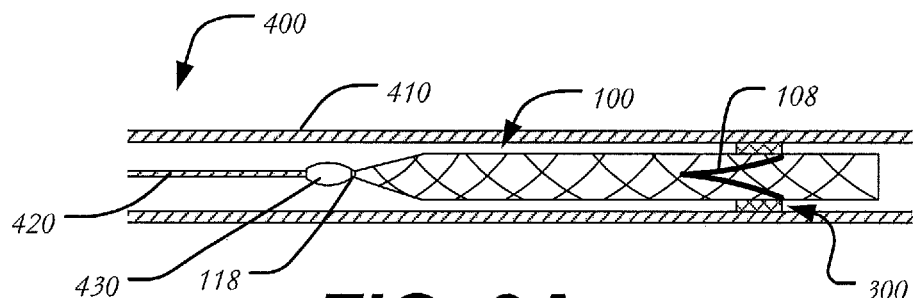
FIGS. 8A-D illustrate the use of conformable band and the process of sealing a heart valve within a native valve annulus.
Figure 8B:
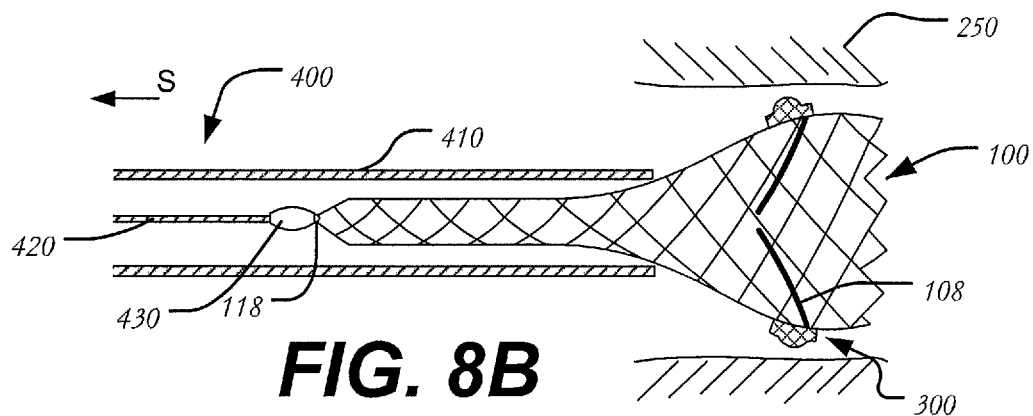

Once heart valve 100 has reached the desired site of deployment, outer sheath 410 may be retracted toward the distal end of catheter 400 in the direction of arrow S to expose heart valve 100 (FIG. 8B). Heart valve 100 remains coupled to inner shaft 420 and begins to expand within native valve annulus 250 as outer sheath 410 is retracted. FIG. 8B illustrates an intermediate position where heart valve 100 is expanding within native valve annulus 250.

Figure 8C:
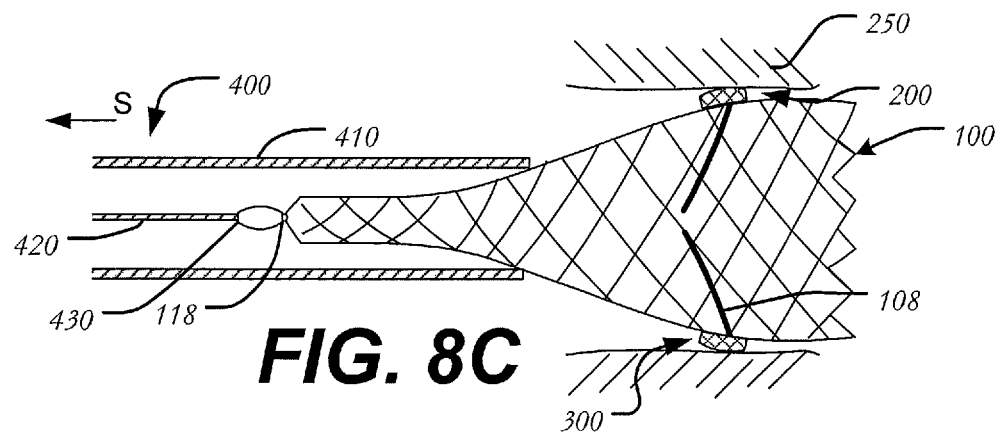

As outer sheath 410 is further retracted, more of heart valve 100 is exposed and heart valve expands further into the native valve annulus 250. As seen in FIG. 8C, conformable band 300 has contacted the walls of native valve annulus 250, and begins to fill any gaps 200 between heart valve 100 and native valve annulus 250.

Figure 8D:
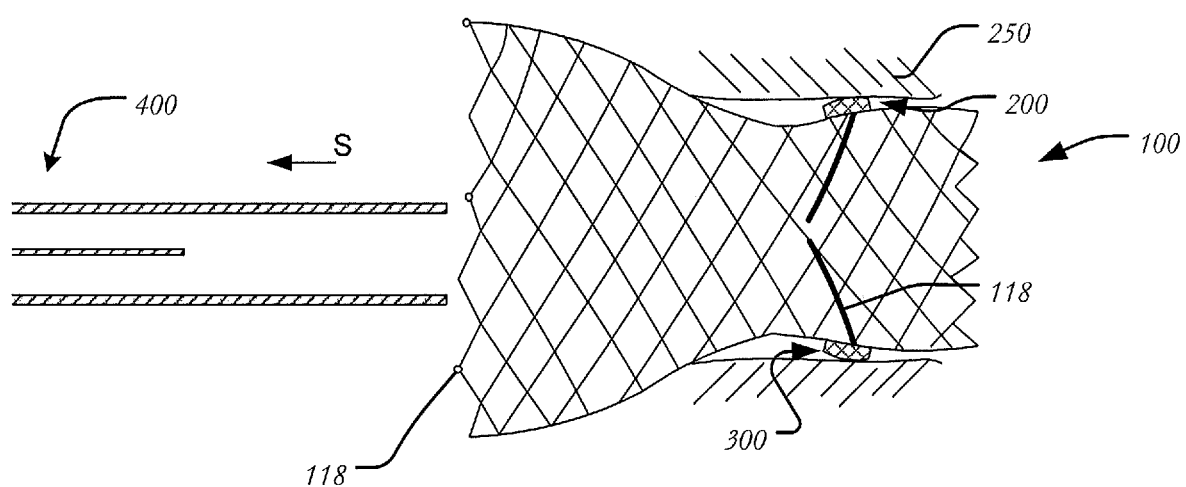

Retaining elements 118 may be disconnected by being moved radially outward from receiving elements of accepting member 430 to free the heart valve 100 from catheter 400. FIG. 8D illustrates heart valve 100 in its fully expanded state with conformable band 300 fully filling the gaps 200 between fully-expanded heart valve 100 and native valve annulus 250. Catheter 400 may then be retracted in the direction of arrow S and removed from the patient. As discussed above, conformable band 300 may promote tissue growth along and on the conformable band to seal the heart valve within the native valve annulus. Alternatively, conformable band 300 may be sufficiently dense (e.g. through the use of polyester fibers or polyester fabric) to adequately seal the heart valve without the need for major tissue growth about the conformable band. When conformable band 300 is functioning properly, the heart valve will be adequately sealed so that blood will flow through the interior of heart valve through valve assembly 105 only and not through any gaps formed between the heart valve and the native valve annulus.

It will also be noted that while the inventions herein are predominately described in connection with the replacement of a tricuspid valve, the inventions are equally applicable to the replacement of other valves, including a bicuspid valve, such as the mitral valve. Moreover, the stent could have different shapes, such as a flared or conical annulus section, a less-bulbous aortic section, and the like, and a differently shaped transition section. Additionally, though the conformable band has been described in connection with expandable transcatheter aortic valve replacement, it may also be used in connection with surgical valves, sutureless valves and other device where sealing is between the periphery and body tissue. Though a transfemoral approach has been described, it will be understood that a transapical or any other suitable approach for implanting the heart valve may be used.

Moreover, although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

It will be appreciated that the various dependent claims and the features set forth therein can be combined in different ways than presented in the initial claims. It will also be appreciated that the features described in connection with individual embodiments may be shared with others of the described embodiments.

In some embodiments, a prosthetic heart valve includes a collapsible and expandable stent having a proximal end and a distal end, a cuff coupled to the stent, a valve assembly including a plurality of leaflets coupled to at least one of the stent or the cuff and a conformable band having an inner surface disposed near the perimeter of the stent adjacent the plurality of leaflets and an outer surface adapted for contacting body tissue, the conformable band being configured to seal the valve assembly against leakage by filling gaps between the prosthetic heart valve and the body tissue.

In some examples, the conformable band may include at least one of a metallic mesh, a braided nitinol mesh or a shape-memory material. The conformable band may be constructed in the shape of a toroid. The conformable band may further include polyester fiber intertwined with the metal mesh to increase density of the conformable band. The conformable band may further include a polyester fabric intertwined with the metal mesh to increase density of the conformable band. The stent may include a plurality of struts and the conformable band is coupled to at least one of the plurality of the struts of the stent.

In some examples, the conformable band may be coupled to an inner surface of the stent. The cuff may have a lumenal surface and an ablumenal surface and the conformable band may be coupled to the ablumenal surface of the cuff. The conformable band may have a non-circular cross-section. The conformable band may have varying heights along the perimeter. The conformable band may include a biological agent for promoting tissue growth. The conformable band may include a chemical agent for promoting tissue growth. The conformable band may be continuously formed about the perimeter of the stent. The conformable band may include at least two rings formed about the stent.

In some embodiments, a method of sealing a prosthetic heart valve in a patient includes positioning the prosthetic heart valve within body tissue, the prosthetic heart valve comprising (i) a collapsible and expandable stent, (ii) a valve assembly including a plurality of leaflets coupled to the stent and (iii) a conformable band having an inner surface disposed about the plurality of leaflets and an outer surface adapted for contacting body tissue, and expanding the stent until the conformable band is in sealing contact with the body tissue.

In some embodiments, a prosthetic heart valve includes a collapsible and expandable stent having a proximal end and a distal end, a valve assembly including a plurality of leaflets coupled to the stent, and a conformable band disposed about the stent between the proximal and distal ends thereof, the band adapted for creating a fluid seal about the circumference of the stent with an adjacent body tissue. In some examples, the conformable band may be attached about an outer surface of the stent.

In some examples, the conformable band may be attached about an inner surface of the stent. The conformable band may be disposed adjacent the plurality of leaflets. The conformable band may include at least two rings formed about the stent. The band may include an inner surface disposed concentric with a perimeter of the stent.

The invention claimed is:

1. A method of sealing a prosthetic heart valve in a patient, comprising:
   positioning the prosthetic heart valve within body tissue, the prosthetic heart valve including (i) a collapsible and expandable stent, (ii) a valve assembly including a plurality of leaflets, and (iii) a first conformable band including a plurality of discrete beads extending around a circumference of the stent, wherein the plurality of discrete beads are connected to one another via junctions; and
   expanding the stent until the plurality of discrete beads are in sealing contact with the body tissue.

2. The method of claim 1, further comprising the step of positioning the prosthetic heart valve within a delivery catheter.

3. The method of claim 2, wherein the prosthetic heart valve is coupled to an inner shaft of the delivery catheter.

4. The method of claim 2, further comprising the step of inserting the delivery catheter into the patient.

5. The method of claim 4, during the step of inserting the delivery catheter, the prosthetic heart valve is collapsed.

6. The method of claim 3, further comprising the step of retracting an outer sheath of the delivery catheter to expose the prosthetic heart valve.

7. The method of claim 6, wherein during the step of retracting the outer sheath, the prosthetic heart valve expands.

8. The method of claim 1, wherein the first conformable band is configured for tissue growth on the first conformable band.

9. The method of claim 1, wherein during the step of expanding the stent, the plurality of discrete beads fills gaps between the stent and the body tissue.

10. The method of claim 1, wherein the step of expanding includes self-expanding the stent.

11. The method of claim 1, wherein the prosthetic heart valve includes a cuff coupled to the stent.

12. The method of claim 11, wherein the cuff includes a first edge and a second edge, and the first conformable band is disposed between the first edge and the second edge of the cuff.

13. The method of claim 11, wherein the first conformable band and the cuff comprise different materials.

14. The method of claim 1, wherein the first conformable band has a toroid-shape.

15. The method of claim 1, wherein the prosthetic heart valve includes a second conformable band.

16. A method of sealing a prosthetic heart valve in a patient, comprising:
- positioning the prosthetic heart valve within body tissue, the prosthetic heart valve including (i) a collapsible and expandable stent, (ii) a valve assembly including a plurality of leaflets, and (iii) a first conformable band including a plurality of discrete beads extending around a circumference of the stent, the plurality of distinct beads defines a plurality of alternating peaks and valleys; and
- expanding the stent such that the plurality of beads fill gaps between the stent and the body tissue.

17. The method of claim 16, wherein the prosthetic heart valve includes a second conformable band.

18. The method of claim 16, further comprising the step of positioning the prosthetic heart valve within a delivery catheter.

* * * * *